United States Patent
Thompson

Patent Number: 5,860,423
Date of Patent: Jan. 19, 1999

[54] ANKLE-FOOT ORTHOSIS

[76] Inventor: Terry Thompson, 901 State Route 46, Columbiana, Ohio 44408

[21] Appl. No.: 761,493

[22] Filed: Dec. 6, 1996

[51] Int. Cl.[6] ..................................................... A61F 5/37
[52] U.S. Cl. ................................ 128/882; 602/23; 602/27
[58] Field of Search .................................. 128/846, 882, 128/869; 602/23, 24, 27, 28, 60, 61, 62, 63

[56] References Cited

U.S. PATENT DOCUMENTS

| | | | |
|---|---|---|---|
| 604,044 | 5/1898 | Hamel | 602/27 |
| 839,223 | 12/1906 | Stevens | 602/27 |
| 1,691,235 | 11/1928 | Fischer | 128/80 |
| 2,439,100 | 4/1948 | Richards | 128/80 |
| 2,584,101 | 1/1952 | Goffredo | 128/80 |
| 2,847,991 | 8/1958 | Andrews | 128/80 |
| 2,874,690 | 2/1959 | Cowgill | 128/80 |
| 2,888,016 | 5/1959 | De Lamater | 128/260 |
| 3,050,053 | 8/1962 | Peckham | 128/80 |
| 3,073,305 | 1/1963 | Biggs, Jr. et al. | 128/166 |
| 3,086,521 | 4/1963 | Desai | 602/27 |
| 3,713,437 | 1/1973 | Wiedmer | 128/25 R |
| 3,804,085 | 4/1974 | Eshuis et al. | 128/85 |
| 3,986,501 | 10/1976 | Schad | 128/80 E |
| 4,289,122 | 9/1981 | Mason et al. | 128/80 E |
| 4,329,982 | 5/1982 | Heaney | 128/80 E |
| 4,566,447 | 1/1986 | Deis | 128/80 E |
| 4,597,395 | 7/1986 | Barlow et al. | 128/80 H |
| 4,621,648 | 11/1986 | Ivany | 128/80 H |
| 4,646,726 | 3/1987 | Westin et al. | 128/80 H |
| 4,649,939 | 3/1987 | Curtis | 128/80 H |
| 4,729,370 | 3/1988 | Kallassy | 128/166 |
| 4,817,589 | 4/1989 | Wertz | 602/28 |
| 5,088,480 | 2/1992 | Wang | 602/23 |
| 5,257,969 | 11/1993 | Mance | 602/28 |
| 5,277,699 | 1/1994 | Williamson | 602/28 |
| 5,431,624 | 7/1995 | Saxton et al. | 602/27 |
| 5,472,411 | 12/1995 | Montag | 128/882 |
| 5,486,157 | 1/1996 | DiBenedetto | 602/27 |

OTHER PUBLICATIONS

Orthopaedic Appliances Atlas, vol. 1, J. W. Edwards—Ann Arbor, Michigan—1952.

*Primary Examiner*—Michael A. Brown
*Attorney, Agent, or Firm*—Penrose Lucas Albright

[57] ABSTRACT

The upper part of a brace is concave to receive a human calf and extends forwardly at either side of the calf. Elastic straps extend from the upper right and left sides of the brace downwardly to the top outside of a modified conventional shoe to support the shoe from plantarflexion as well as inversion and eversion. The lower end of the brace is removably and pivotally connected to the heel curve of the shoe.

12 Claims, 8 Drawing Sheets

ANKLE-FOOT ORTHOSIS

FIELD OF THE INVENTION

This invention relates to an ankle-foot orthosis. More specifically, the invention relates to a device which is attached to the user's calf and shoe to prevent uncontrolled plantarflexion, inversion and eversion of the foot while walking.

BACKGROUND OF THE INVENTION

Drop foot is characterized by an insufficient control to check plantarflexion, inversion and/or eversion of the foot while walking. Consequentially, a victim suffering from drop foot walks with the toe of an affected foot dragging along the ground. Further, the affected foot may twist inversionally or eversionally. Either or both symptoms provide a sufferer of drop foot with an embarrassing and unsafe gait. Generally, drop foot is incurred by stroke victims, multiple sclerosis patients and/or those suffering from neurological, muscular and/or orthopedic pathological conditions. Victims of any of these pathological conditions can be especially prone to medical complications which may result from a fall caused by tripping due to the drop foot stride.

Drop-foot and similar pathological conditions can be corrected utilizing an appropriate ankle-foot orthosis. Moreover, in many cases, by utilizing an appropriate ankle-foot orthosis in a therapeutic rehabilitation program, the patient can be cured of at least the symptomatic gait associated with drop-foot.

It is advantageous for a therapeutic rehabilitation program to include the patient's normal daily routine, such as walking while involved in working or social situations. In this case, the ankle-foot orthosis should not only be effective in correcting foot drop, but also comfortable to wear and not overly conspicuous so as not to draw attention to the infirmity or otherwise embarrass the patient. Further, an appropriate drop-foot orthosis should be relatively inexpensive, not requiring the patient to acquire different sets of shoes (which can be used only during rehabilitation due to differing sizes), and adaptable to a wide variety of shoe styles. Still further, the ankle-foot orthosis should be adjustable to be applicable to a wide variety of orthopedic needs and rehabilitation stages. In light of the circumstance that many drop-foot patients suffer from pathological conditions also affecting their dexterity, the ankle-foot orthosis should also be simple to use.

Before the present invention, there has been no ankle-foot orthosis design that successfully and fully addresses these concerns. Many attempted to provide a static stop to prevent any plantarflexion, such as Mason et al.'s U.S. Pat. No. 4,289,122 and Goffredo's U.S. Pat. No. 2,584,010, but these devices have proved, in many cases, to aggravate the patient's condition since the muscles used for plantarflexion tend to atrophy from disuse. Mason et al., as well as other devices, such as Shad's U.S. Pat. No. 3,986,501, require a larger than normal-size shoe to accommodate the brace, and necessitate the leg's intimate and extensive contact with the brace which increases the user's discomfort. Further, in Goffredo and Shad, methods of applying the orthosis to the foot challenge a patient's dexterity. Furthermore, these devices, like those of Heaney's U.S. Pat. No. 4,329,982 and Deis' U.S. Pat. No. 4,566,447, do not address lateral (laterally outward) or medial-lateral (laterally inward) support of the foot. Although lateral support is addressed in Wertz's U.S. Pat. No. 4,817,589, Wertz discloses a lever arm which is too short for either effectively encouraging dorsiflexion or discouraging plantarflexion. Also, Wertz's support member is unstably secured to the leg and may slip from its relative position due to the movement of the foot, destroying the brace's potential effectiveness, since it is merely held firm to the back of the leg via the elastic straps. Furthermore, none of these orthosises provides for ease in adjustability of their supports. Von Baeyer's drop foot brace, as illustrated on page 426, FIG. 700 of the *Orthopaedic Appliances Atlas*, Volume I (1952), although providing sufficient moment arm and ease of adjustability for its elastic supports, which encourage the dorsiflexion of the foot and control the lateral or medial-lateral deflection of the foot, appears to provide for intimate contact of the foot with the straps by securing the straps inside the shoe, and further appears to provide at least one static stop for plantarflexional motion.

SUMMARY OF THE INVENTION

The present invention provides an ankle-foot orthosis which effectively resists uncontrolled plantarflexion of the foot by utilizing elastic straps which are attached at one end to the forward dorsum of a modified conventional shoe and are anchored at the other end, above and rearwardly, to a brace which projects forward of the calf, above the shoe. The straps are attached to either side of the exterior of the shoe and are anchored above on the brace to either side of the calf; thus, the straps are also disposed to provide resistance to uncontrolled medial-lateral or lateral motion, such as, respectively, inversion or eversion. Also, the straps are adjustable to permit adjustment of the orthosis to the patient's needs.

The brace is pivotally attached to the back of the shoe and is affixed to the calf by a belt wrapped around the calf and brace. For the patient's comfort, the leg's direct contact with the orthosis is minimal, normally only the area at the belt and at least part of the back of the calf above the belt, since the brace is supported on the shoe at the apex of the shoe's heel curve at the back of the shoe and extends vertically upward therefrom. Easy on/off methods of attachment are utilized in this orthosis, such as snap buttons and hook-and-eyes, that do not overly challenge most patients' dexterity.

The orthosis of the present invention utilizes a conventional street shoe, which can be the patient's own shoe which lie or she normally wore before obtaining this orthosis. The shoe need only be slightly modified by the addition of three or four attachment means for the brace and straps, modifications which well-known methods can easily accomplish.

The brace can be easily and quickly removed from the shoe, which is advantageous in a variety of social and therapeutic settings, having in mind, of course, the patient's safety and recovery. Further, the shoe retains an aesthetic appearance, since connection means for the brace and the straps on the shoe need not be overtly conspicuous and can appear ornamental or be of the same color as the shoe or be covered. Thus, the patient is spared the sacrifice of forswearing considerations of comfort, style and cost in purchasing an appropriate shoe for use with the orthosis because nearly any comfortable shoe is suitable for use with the orthosis of the present invention and the shoe's aesthetic appearance is not substantially affected by the minor modification required to make the shoe compatible with the orthosis.

The patient can conceal the orthosis of the present invention with a sufficiently long trouser or slack leg or a sufficiently long skirt. Parts of the orthosis which would normally come into view, such as the sections of the straps attached to the top of the shoe and the section of the brace attached to the back of the shoe, are camouflaged by utilizing material in these areas which blend with the shoe material. The straps can be criss-crossed over the shoe which not only provides improved support but arranges the straps so they do not unduly deform a trouser or slack leg.

Especially advantageous in therapy, the patient can thus wear this orthosis in a wide variety of environments, i.e.—at work, play, while exercising or at leisure, without being self-conscience, or unnecessarily forsaking fashionable styles, or feeling a loss of comfort.

DESCRIPTION OF THE PREFERRED EMBODIMENTS

Referring to FIGS. 1 through 6, ankle-foot orthosis 18 utilizes brace 21 and conventional shoe 24 in a cooperative relationship to provide relief from drop-foot, lateral or medial-lateral instability and other orthopaedic dysfunctions.

Figure 1:
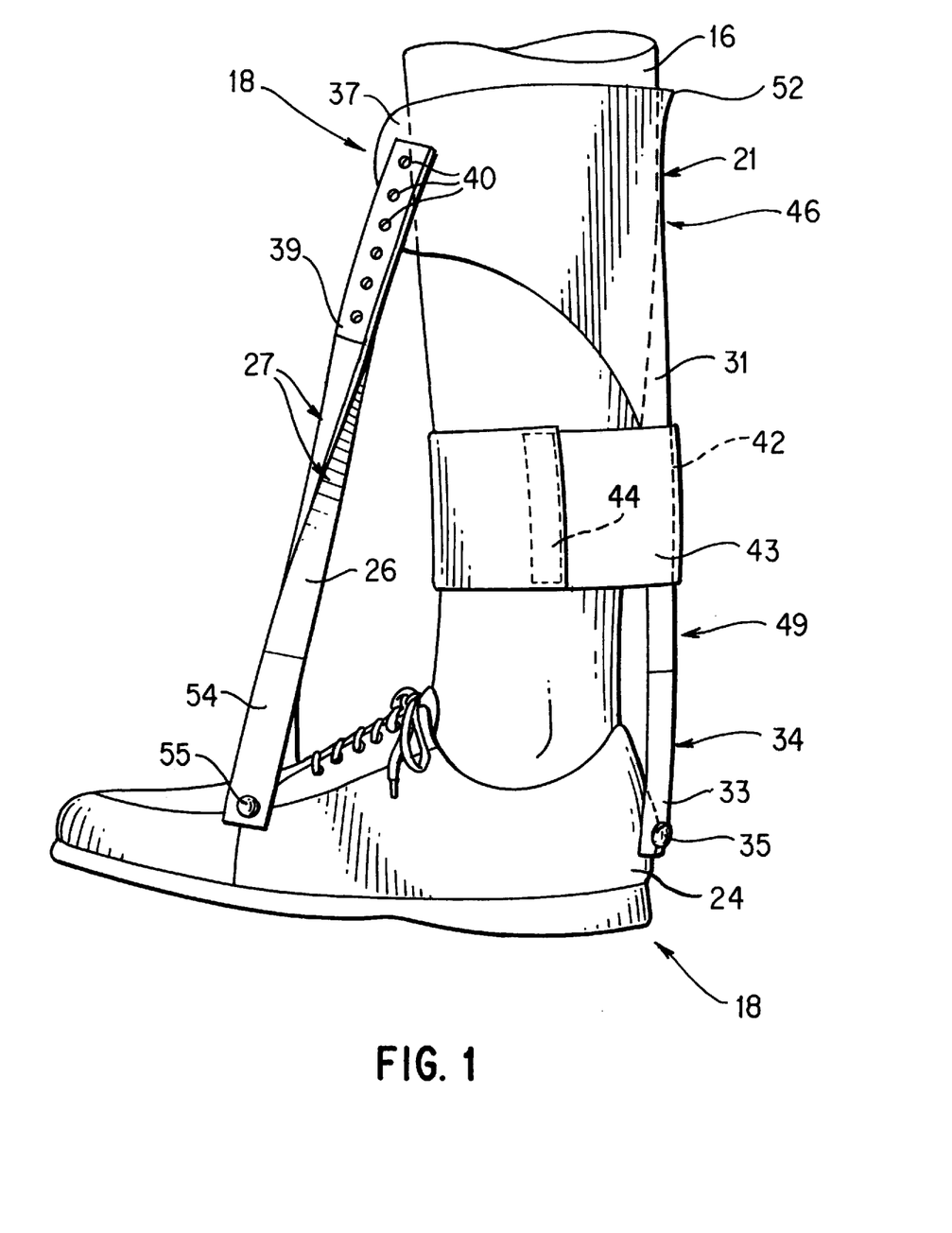
FIG. 1 is an elevational profile view of the present invention as assembled and worn on a left leg or foot.

As seen in FIG. 1, brace 21 is pivotally attached to the back end of shoe 24 proximate to the apex of the heel curve of shoe 24 and vertically laterally and medial-laterally supports the forward portion of shoe 24 via elastic straps 27. Brace 21 also comprises vertical member 31, pivoting connector 34, forward extending portions 37 (shown particularly in FIGS. 2a and 3a), adjustable attachments 40 (one-half of which is attachment 40b shown particularly in FIG. 3a, the other half of which is attachment 40a shown particularly with either strap 27 in FIGS. 2c and 3c) and belt 43 (shown particularly in FIGS. 2d and 3d).

The forward part, forward portion or forepart of shoe 24 described herein and in the claims refers to the portion of shoe 24 which, when shoe 24 is worn on foot 16, is forward of the ankle. The back end, back part, rear or rearward part of shoe 24 described herein and in the claims refers to the most rear portion of shoe 24 which, when shoe 24 is worn of foot 16, is behind the back of foot 16 and includes the heel curve.

Figure 4:
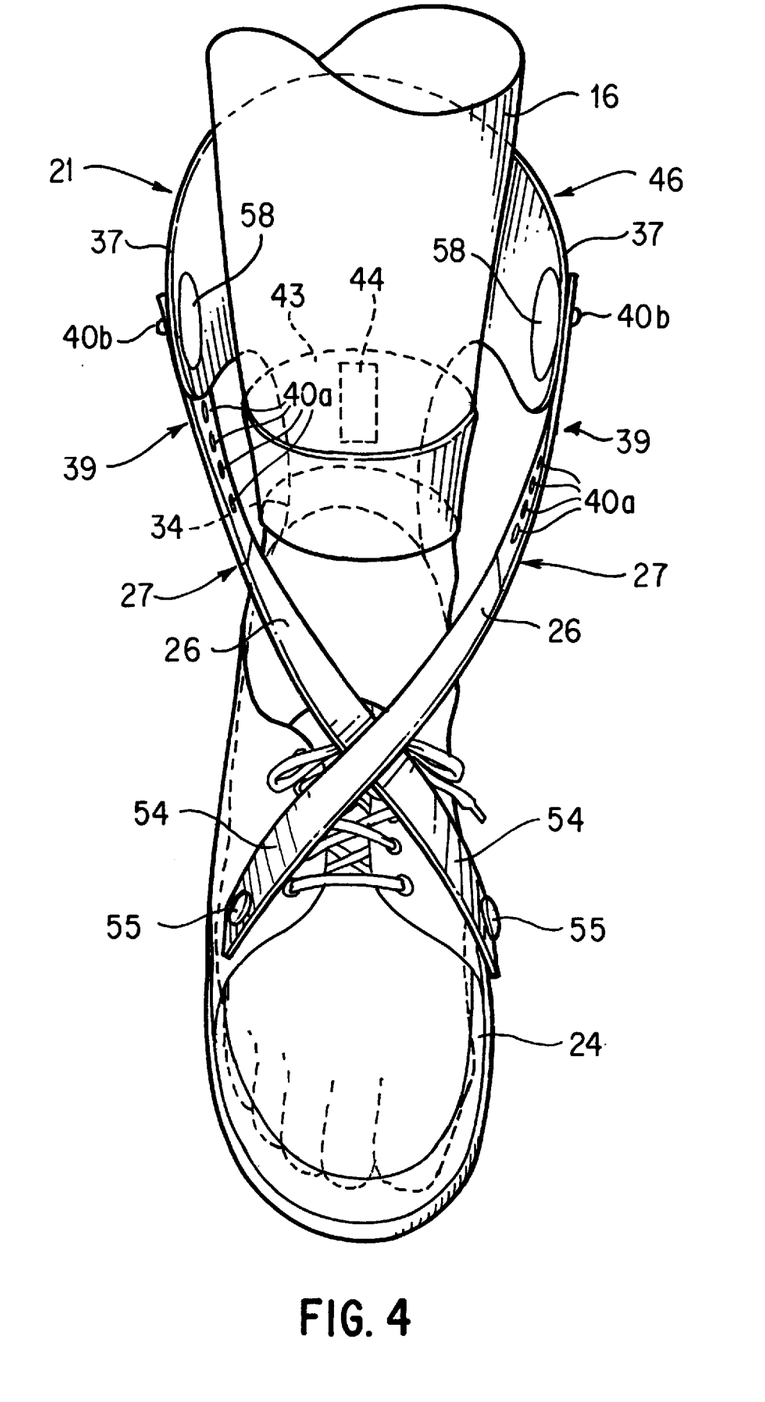
FIG. 4 is a top and front perspective view of the present invention as assembled and worn.
Figure 5:
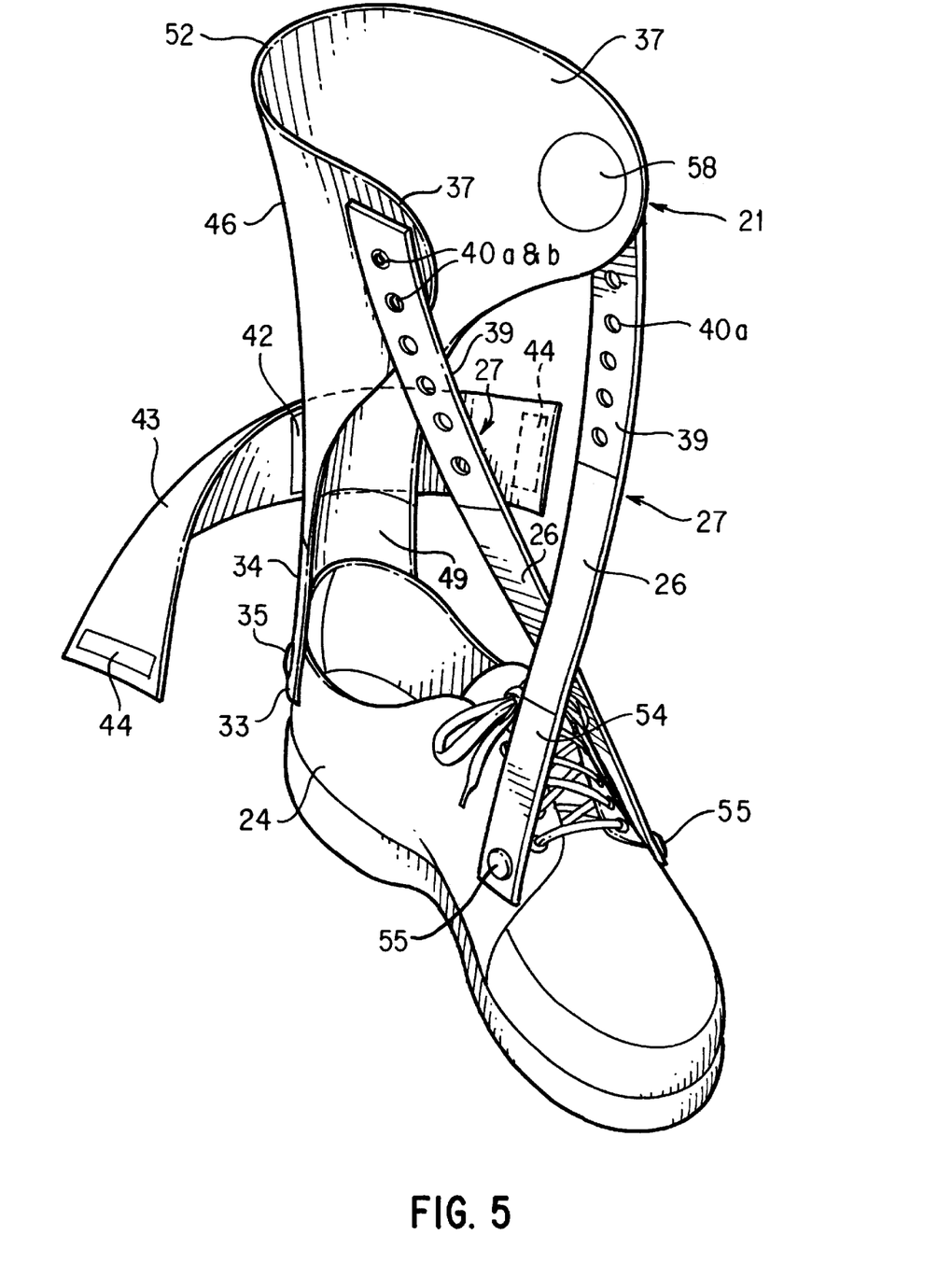
FIG. 5 is a three-quarter perspective view showing the top, front and right partial views of the present invention which is assembled but not being worn.

Vertical member 31 is preferably composed of substantially rigid thermosetting plastic, such as thin-sheeted polypropylene material, molded to form an upper portion 46 and a shank 49. Referring to FIGS. 4 and 5, upper section 46 curves concavely laterally partially around, so as to embrace, the rear and sides of part of leg 16 of the wearer, at his or her mid or upper calf 16, and to project forwardly therefrom to form forward extending portions 37 which are disposed forward of and to either side of the mid or upper calf 16. The top of upper portion 46 bends rearwardly at the incurvature of the concave to form lip 52 (also shown in FIG. 1). Lip 52 prevents to top edge of brace 21 from biting into or otherwise providing discomfort to the adjacent back portion of leg 16.

Figure 6:
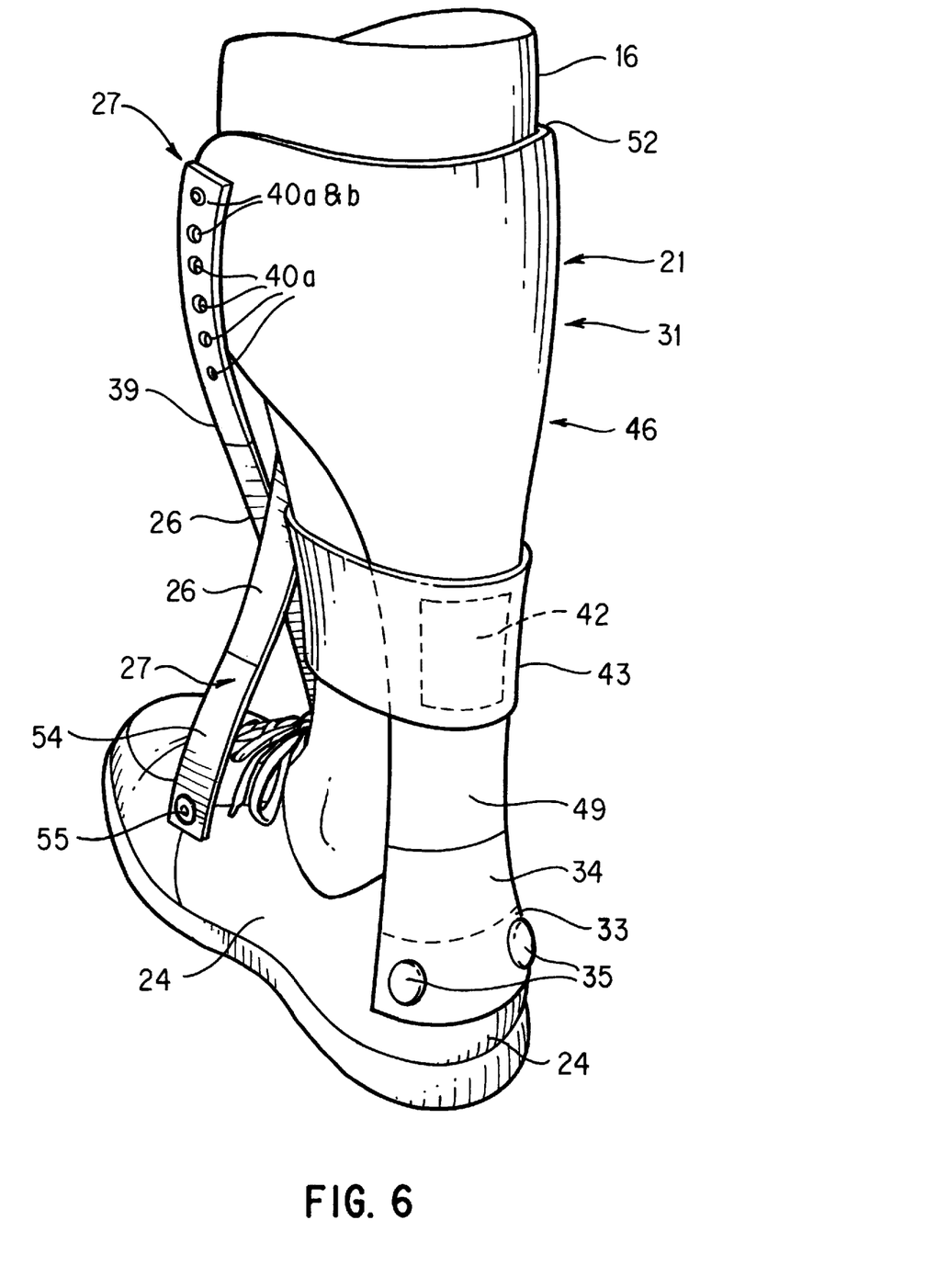
FIG. 6 is a rear three-quarter perspective showing the top, back and left partial views of the present invention which is assembled and being worn.

Referring again to FIGS. 1 through 3 and also to FIG. 6, vertical member 31 extends downwardly from upper portion 46 and narrows to form shank 49. Shank 49 extends downwardly to a tapered end slightly above the apex of the heel curve of shoe 24. Belt 43 is attached to the top of shank 49, just below upper portion 46, on the outside of vertical member 31, that is, the side of vertical member 31 which faces away from leg 16 of the user. Preferably, belt 43 is composed of a sturdy clothe-like material, such as nylon, aid is removably affixed to vertical member 31 via a Velcro®-like attachment means 42 in a suitable manner so that belt 43, wrapped around the adjoining portion of calf 16, substantially fixes the disposition of orthopaedic brace 21 in relation to calf 16. Belt 43 is securely fastened to itself via a further Velcro®-like attachment means 44.

The side of vertical member 31 which faces leg 16 of the user, that is, its inside, is preferably finished smoothly and the edges of vertical member 31 are preferably rounded so that neither the inside finish nor the edges provide a potential source of discomfort to the user.

A pivoting connector 34 is attached to the bottom of shank 49 and, in turn, attaches ordiopaedic device 21 to the back of shoe 24. Pivoting connector 34 provides means for brace 21 to be affixed to the outside of shoe 24, at the apex of the heel curve of shoe 24, while permitting dorsiflexor and plantflexor pivoting of shoe 24 with respect to brace 21. Since brace 21 is connected proximate the apex of the heel curve of shoe 24 (the most rearward point of shoe 24) and extends vertically upwardly therefrom to contact the calf proximate the posterior ruga (the section of the calf which protrudes rearwardly), most of shank 49 (at least below belt 43) is normally spaced from the back of the calf from the area of the ankle up to proximate the posterior ruga.

Figure 3A:
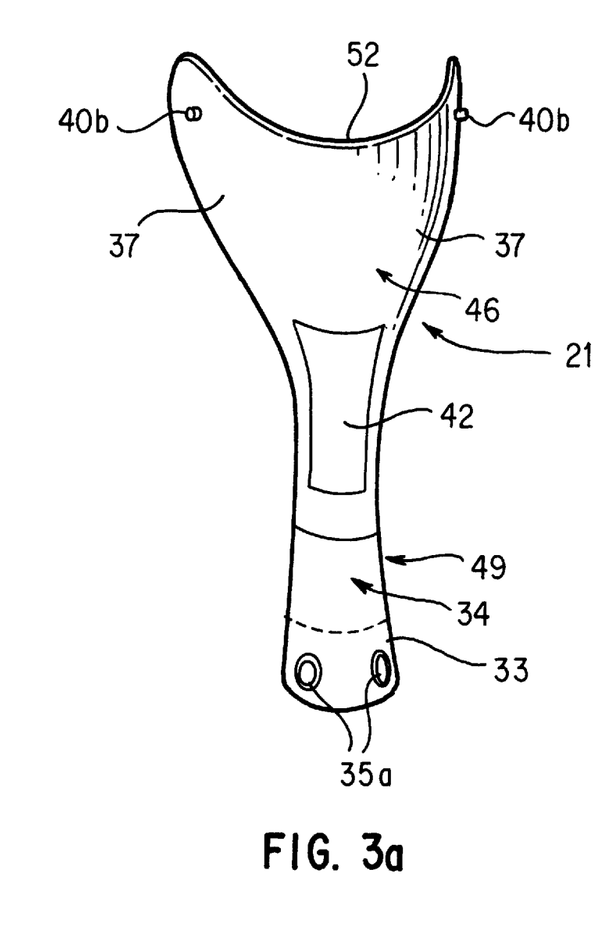
FIG. 3a is an elevational back view showing a vertical brace utilized in the present invention.
Figure 3B:
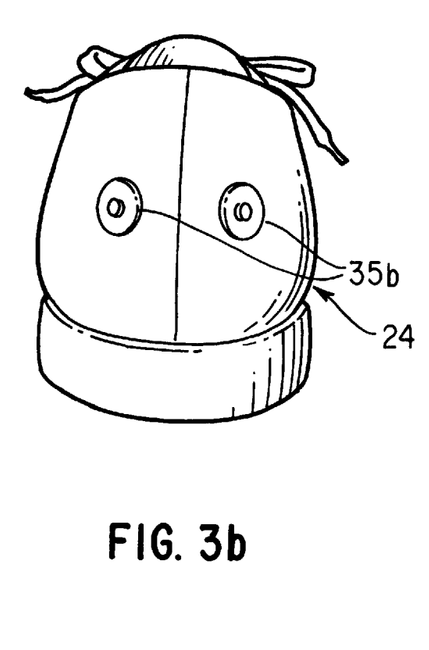
FIG. 3b is an elevational back view showing the back of a modified shoe utilized in the present invention.

In the preferred embodiment, hinged connection means 34 is removably connected to the back-part of shoe 24, assists in stabilizing lateral and medial-lateral motion of the foot, prevents lateral and medial-lateral tilt of brace 21 with respect to shoe 24, and provides an appearance which aesthetically blends with the appearance of shoe 24. Pivoting connector 34 is preferably a leather-like sheath which envelopes the bottom section of shank 49 and extends downwardly therefrom to form hinge 33 with resilient connectors 35a or dual sockets 35a (seen in FIGS. 2a and 3a) of dual snap buttons 35 affixed thereon. Dual sockets 35a are disposed on hinge 33 appropriately below the tapered end of shank 49 on a horizontal plane and a short equal distance to either side of the vertical axis of brace 21. Dual sockets 35a disposed on hinge 33 are one operative half of connections means 35. The other half of connections means 35, seen in FIG. 3b, are resilient connecting members 35b or dual balls 35b. Resilient connectors 35b are appropriately disposed horizontally across a plane longitudinally bisecting shoe 24, at the apex of the heel curve of shoe 24 and arranged for operative receipt of resilient connectors 35a.

Dual snap buttons 35 are an example of an appropriate resilient connecting member 35 because they provide secure but removable attachment of brace 21 to shoe 24. Also, this resilient connection means 35 assists the lateral and medial-lateral stability of shoe 24. Moreover, dual snap connectors 35 prevent lateral and medial-lateral tilting of brace 21 with respect to shoe 24. Dual snaps 35 are easily arranged and permanently attached (via well-known methods) to the back of shoe 24 and to hinge 33 and thereby provide an appropriate secure, but resilient, connection 35 between the back of shoe 24 and bottom of brace 21 which permits dorsiflexor and plantarflexor pivoting of shoe 24 with respect to brace 21.

Two straps 27, which are substantially identical to the other, are each attached to the exterior of a respective forward extending portion 37 and supporting, via attachment to the exterior of shoe 24 proximate the bottom ends of straps 27, the forward part. Each strap 27 has a bottom section 54, a middle elastic section 26 and a top section 39. Straps 27 provide elastic connection means 27 for elastic support of shoe 24.

Figure 2C:
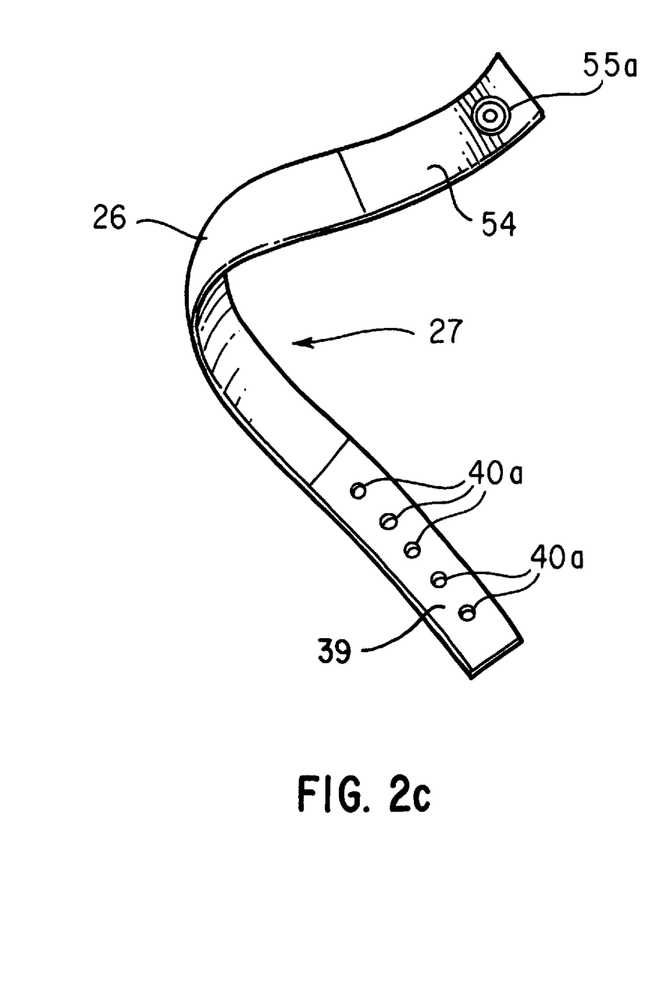
FIG. 2c is a front elevational view showing one of the two identical straps utilized in the present invention.
Figure 2D:
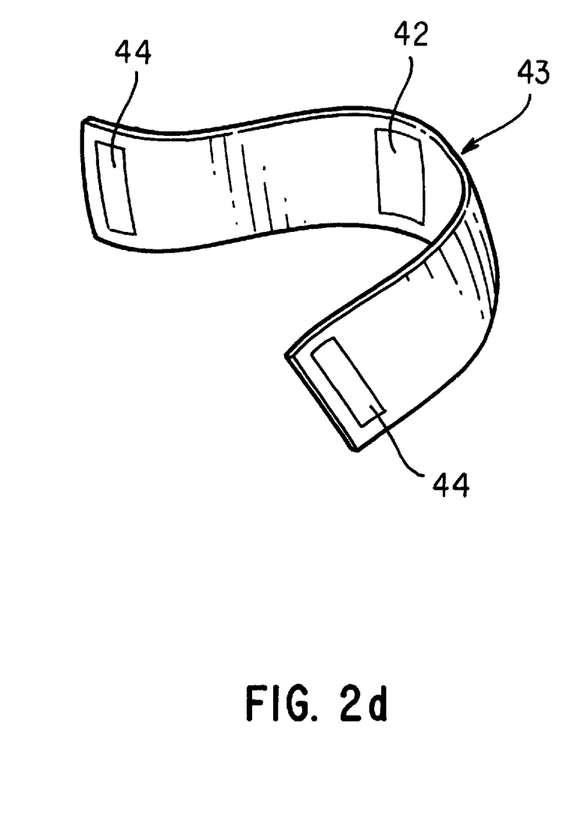
FIG. 2d is a front elevational view showing a belt utilized in the present invention.
Figure 3C:
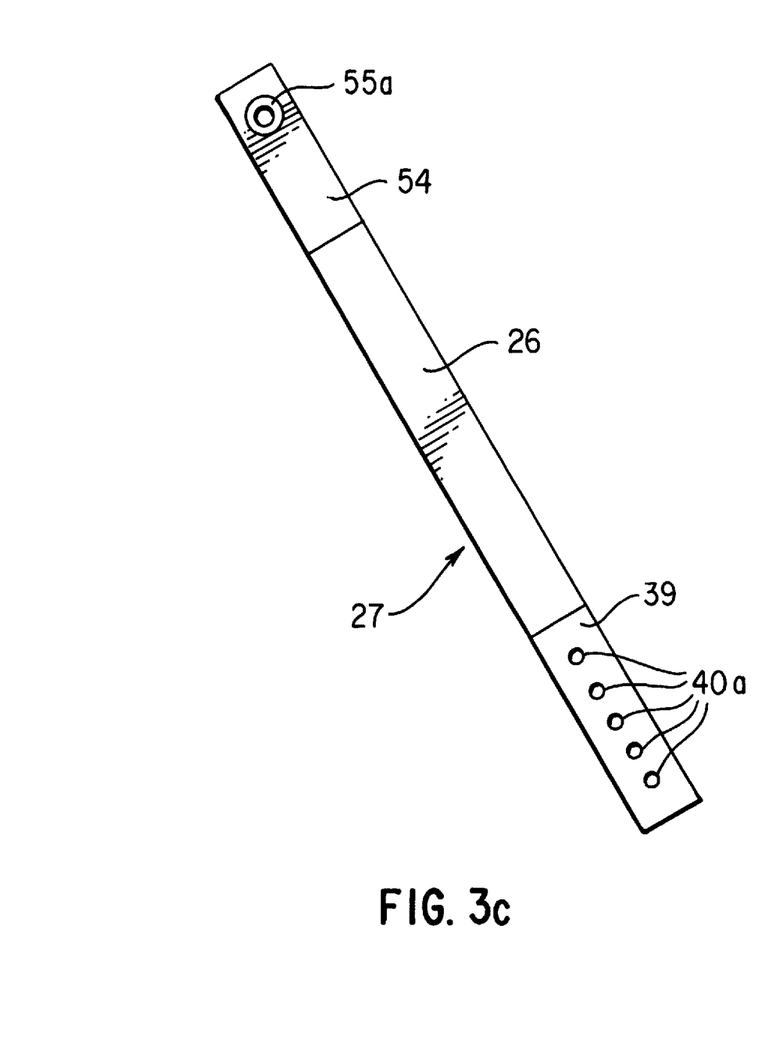
FIG. 3c is an elevational back view showing one of the two identical straps utilized in the present invention.
Figure 3D:
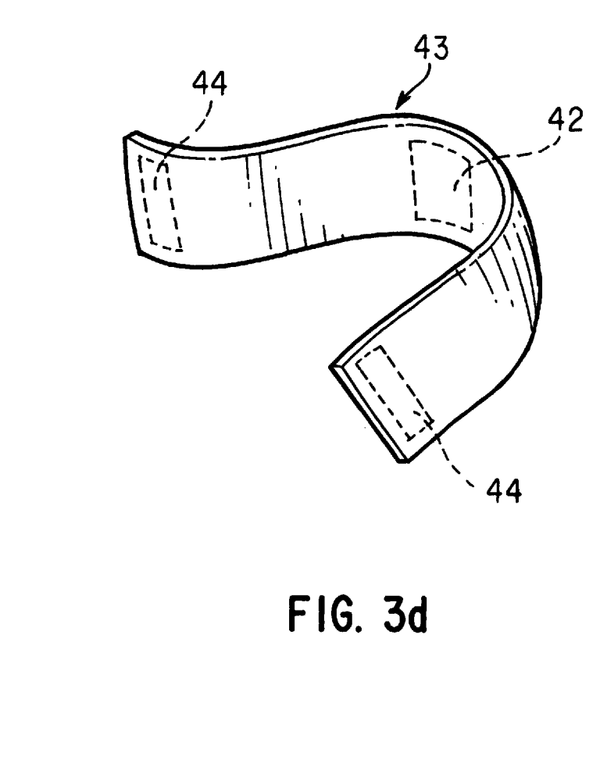
FIG. 3d is an elevational back view showing a belt utilized in the present invention.

Bottom section 54 is composed of a leather-like material 1or durability and flexibility. Referring to FIGS. 2c and 3c, resilient connection member 55a is disposed on bottom section 54, near its bottom end, and is an operative half of connection means 55.

Figure 2A:
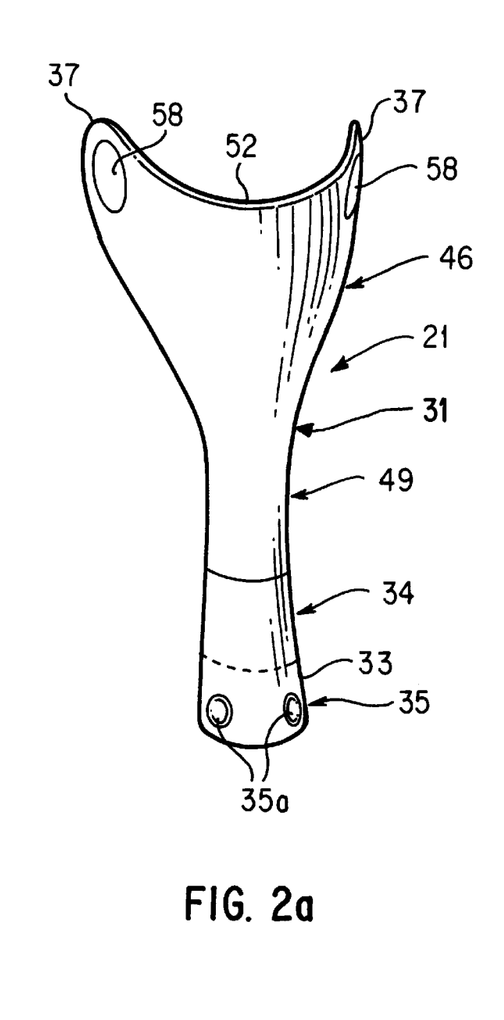
FIG. 2a is a front elevational view showing a vertical brace utilized in the present invention.
Figure 2B:
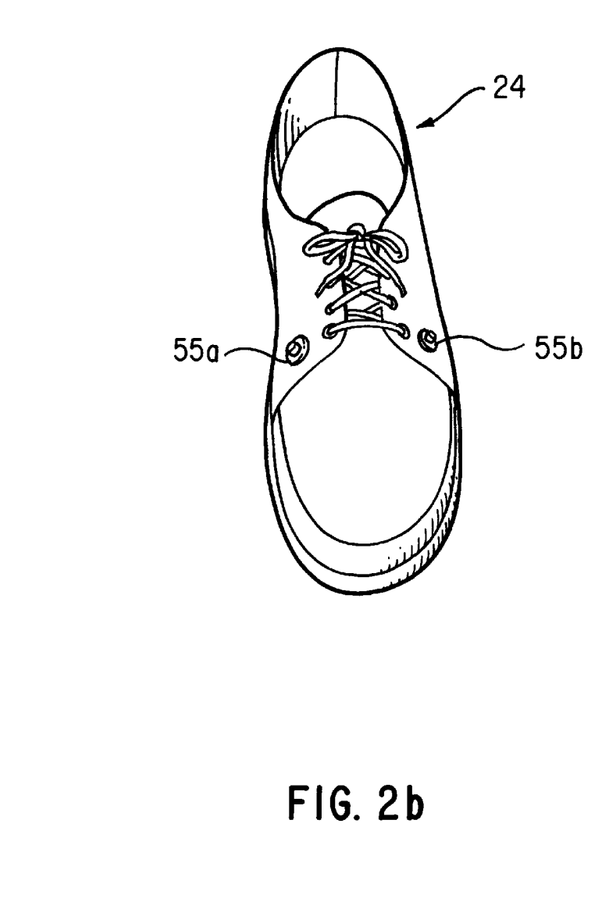
FIG. 2b is a perspective view showing the top and front of a modified shoe utilized in the present invention.

Referring to FIG. 2b, the other operative half of connection means 55, which is resilient connection member 55b, is disposed on the exterior of shoe 24, on the forward section of shoe 24. One connection 55b is affixed to each side of the forward part of shoe 24, appropriately for receiving a respective connector 55a (each side of shoe 24 being defined by a vertical longitudinal plane which bisects shoe 24 into substantially equal left and right parts). Preferably, resilient connection member 55 provides a secure but removable attachment of its respective strap 27 to the forepart of shoe 24. Connector 55b is easily permanently affixed to shoe 24 through commonplace and well-known methods. The specific disposition of connectors 55b on shoe 24 is determined by the orthopaedic specialist or therapist. Alternatively, the specific arrangement of connectors 55b on shoe 24 is preset at, as an example, the vamp seams on either side of the forepart of shoe 24. Conventionally, connectors 55b are disposed congruent to each other on each side of the dorsum of the forward section of shoe 24 (within a vertical plane which is perpendicular to the aforementioned vertical longitudinal plane and at equal distance from this vertical longitudinal plane). In the figures, connection means 55 is illustrated as a snap button type connection with connectors 55a being sockets and connectors 55b being balls.

Permanently attached to the top end of bottom section 54 and extending upwardly therefrom is elastic section 26. Elastic section 26 provides sufficient strength to support shoe 24 from plantarflexor motion with shoe 24 weighted with the user's foot, as supported by straps 27, and enough elasticity to permit a normal push-off motion of the foot through the effort of the user exercising the respective muscles.

Permanently attached to the top end of middle elastic section 26 is top section 39. Top section 39 is also composed of a leather-like material for durability and flexibility. Top section 39 is adjustably attached to the outside of the respective forward extending portion 37 via adjustable attachment 40. As seen in FIGS. 2c and 3c, preferably, each top section 39 contains at least on anchor 40a which is an operative half of adjustable attachment 40. The other operative half of adjustable attachment 40, seen in FIG. 3a, is attacher 40b, which is appropriately disposed on the outside of each forward extending portion 37. One attacher 40b is permanently affixed to the exterior side of each forward extending portion 37.

In the preferred embodiment, adjustable attachment 40 provides secure but adjustable connection of strap 27 to its respective forward extending portion 37 so that the tautness of strap 27 between its connection 55 and attachment 40 can be increased or decreased for differing therapeutic and social environments. Adjustable attachment means 40 is portrayed in the figures as a hook-and-eye type, with hook 40b centrally disposed on the outside of each forward extending portion 37 and the plurality of eyes 40a, each for receiving hook 40, disposed, one above the other, in a vertical line on the top section 39 of each strap 27. Hook-and-eye type adjustment means 40 provides a simple and easy method of adjusting the elastic strength of orthosis 18 in supporting the foot from plantarflexion, lateral and medial-lateral motions for different therapeutic programs as well as providing the patient with control in these programs.

As shown in FIG. 5, on the inside surface of forward extending portions 37, opposite hooks 40b, and inside shoe 24, opposite snap buttons 35b and 55b, which are respectively on the back and forward portions of shoe 24, protective pads 58 are provided to prevent the anchors of these connection means to cause the wearer discomfort.

Because of its simplicity and ease of fabrication, ankle-foot orthosis 18 is predisposed for a range of manufacturing choices; orthosis 18 can be prefabricated in conventional and generic sizes and equipped with shoes 24 of respective sizes and provided to the patients via health-care and therapeutic specialists or can be provided as a kit wherein orthosis 18 is at an advantageous stage of completion.

For example, orthosis 18 can be provided in a kit in which brace 21 is premolded to fit a large range of sizes of calves and means is also provided to modify the patient's shoe or shoes 24 for connection of brace 21 thereto. Thus, the patient is provided with the opportunity of choosing his or her own shoe 24 or a variety of shoes 24 for use in orthosis 18. Further, due to the ease of forming thermosetting thin-sheeted plastics, vertical member 31 can be customized by a health-care specialist to meet the needs of each patient. Means can also be provided in the kit whereby the position of eyes 40a can be fabricated to calibrate each strap 27 to the needs of the patient. Further still, an appropriate size shoe 24 can be provided in the kit with or without connection means 35b and/or 55b attached to shoe 24.

The leather-like material of pivoting connector 34 and straps 27 can be provided in a variety of colors or be dyed to the specification of the patient so as not to detract conspicuously from the aesthetic appearance of shoe 24.

Referring FIGS. 1, 4 and 6, preferably, orthosis 18 is placed on the foot with brace 21 connected to shoe 24 at connection 35. Preferably, but not necessarily, a knee-length sock is worn. Straps 27 are connected to shoe 24 at connections 55, but are not yet connected to vertical member 31 at connections 40. Shoe 24 is adjusted and secured onto the foot by, for example, shoe laces or buckles. Belt 43 is then snugly placed around the adjoining calf 16 to dispose brace 21 against calf 16. Each strap 27 is then attached to respective forward extending portion 37 to the tautness desired (by adjustable attachment 40) which is most advantageous to the therapy and/or the gait of the patient. For greater elastic support, a strap 27 is connected to its respective forward extending portion 37 at a lower point on the strap 27; for lesser elastic support, a strap 27 is connected to its respective forward extending portion 37 at a higher point on the strap 27.

In the preferred embodiment, strap 27 which is connected to the left side of shoe 24 is attached to the right forward extending portion 27 of brace 21 and strap 27 which is connected to the right side of shoe 24 is attached to the left forward extending portion 27 of brace 21. This crossing of straps 27 enhances the lateral and medial-lateral support of shoe 24, as well as the vertical support, by increasing the tensile reach of each strap 27. Moreover, this disposition of straps 27 provides that a trouser leg is less conspicuously misshapen due to straps 27.

The tensile support of each strap 27 can be advantageously adjusted to meet differing needs of the patient. For example, if the patient requires support from uncontrolled plantarflexional, lateral and medial-lateral movement, each strap 27 can be adjusted to an appropriate tensile support so that straps 27 advantageously support shoe 24, weighted with the foot, in a perpendicular relation to calf 16 and disposed in an appropriate fore and aft plane with calf 16.

In any case, the patient can overcome, by utilizing the appropriate muscles, the support of straps 27 in a plantarflexional, eversional or inversional motion and thus achieve a more nearly normal stride and exercise these muscles. If orthosis 18 is utilized in therapy with the goal of recovery of a more nearly normal unassisted stride, the strength of the support of straps 27 can be advantageously calibrated via adjustment of attachment 40 as the patient progresses or regresses. Orthosis 18 can, of course, be utilized as a permanent brace advantageously utilizing its comfort and aesthetic appearance.

While the patient is walking, straps 27 resist plantarflexion of the foot to a degree which is determined by the adjustment of connecting means 40. Via adjustment of connecting means 40, straps 27 can also encourage dorsiflexion of the foot. The patient performs a push-off motion, as recognized in a normal stride, by appropriately exercising the muscles required for foot plantarflexion with enough force to stretch elastic straps 27. Hinge 33 permits shoe 24 to pivot dorsiflexionally and plantarflexionally while maintaining connection to brace 21 at attachment means 35.

Straps 27 support shoe 24 so as to resist lateral and medial-lateral motion to a degree which is also determined by the adjustment of each connecting means 40 and the circumstance that straps 27 are crossed. As seen in FIGS. 1 and 4 through 6, (with straps 27 crisscrossed over shoe 24), strap 27, which is anchored to the left forward extending member 37 and attached to the right side of shoe 24, resists lateral motion (such as eversion) for the right shoe 24, and medial-lateral (such as inversion) for the left shoe 24. On the other hand, strap 27, which is anchored to the right forward extending member 37 and attached to the left side of shoe 24, resists lateral motion (such as eversion) for the left shoe 24, and medial-lateral (such as inversion) for the right shoe 24. Via proper calibration of each connecting means 40, straps 27 can also advantageously encourage lateral or medial-lateral motion of the foot in one direction. Further, to a certain degree, dual snap buttons 35 assist in resisting lateral and medial-lateral deflection of shoe 24.

Thus, drop-foot or other walking disorders are corrected by proper manipulation and use of orthosis 18. Further, recovery is aided by correct use of orthosis 18 since it provides for advantageously exercising muscles and is to be worn throughout the patient's daily routine.

In adjusting straps 27 it is possible to do completely away with one strap 27 or both and thus provide no elastic support from a respective forward extending portion 37 to a respective side of shoe 24. In this case, the respective connection means 40 and 55 can be omitted. As previously explained, resilient connectors 35 are arranged to either side of a vertical plane which bisects the rearmost portion of shoe 24 into two halves. Thus, resilient connection 35 on the one side of shoe 24 provides that brace 21 (which is laterally anchored by the other resilient connector 35) resists, at this point at the back of shoe 24, twisting deflection of shoe 24 to the other side, albeit to a lesser degree than when a strap 27 is appropriately utilized. Since hinge connection means 34, in the preferred embodiment is laterally flexible to the extent allowed between its contact to the bottom of shank 49 and dual connection 35, the resistance provided to the back of shoe 24 is not static and the appropriate muscles are allowed to be exercised while a more nearly normal stride is imparted by orthosis 18. Therefore, for orthopaedic correction of mild inversion and/or eversion of shoe 24, both straps 27 with connection means 40 and 55 may be omitted in the present invention.

In the figures, shoe 24 is illustrated as a conventional laced street shoe for representative purposes only, and is to be considered to exemplify any footwear which can be advantageously modified with brace 21, such as many types of overshoes, athletic shoes, orthopaedic shoes, as well as laced or laceless conventional street shoes. Further, illustrations of the present invention concerning one foot are to be understood to apply equally to other foot, taking into consideration shape and utility.

Although this invention has been disclosed and discussed primarily in terms of specific embodiments thereof, it should be understood that this description has been given for clearness of understanding only, and no unnecessary limitation should be understood therefrom, for modifications that will be obvious to those, skilled in the art will be within the spirit and scope of the appended claims.

Having disclosed my invention, what I claim as new and to be secured by Letters Patent of the United States is:

1. An ankle-foot orthosis comprising:

a shoe;

a substantially rigid brace;

and at least two elastic straps, said shoe comprising an exterior surface and two sides,
  said exterior surface comprising an upper of said shoe,
  said upper comprising a forepart and a back-part,
  said two sides comprising a left side and a right side,
    said left side disposed to the left of a longitudinal vertical plane which bisects said shoe into two halves,
    said right side disposed to the right of said longitudinal vertical plane which bisects said shoe in said two halves;

said brace comprising a belt for securing said brace to a calf, said brace further comprising a shank and an upper section,
  said shank comprising hinge connection means for pivotal attachment to said back part, said shank extending upwardly from said hinge connection means and connecting integrally with said upper section, said upper section curving laterally around so as to embrace said calf, said upper section comprising two forward extending portions, a forward extending portion disposed to the left and forward of said calf and a forward extending portion disposed to the right and forward of said calf;

each elastic strap of said two elastic straps comprising an upper portion and a lower portion, said upper portion disposed connected to and extended upwardly from said lower portion, said upper portion comprising an attachment means, said attachment means providing means for attaching each said elastic strap to a respective forward extending portion, said lower portion comprising an affixing means, said affixing means connecting said elastic strap to a respective side of said forepart of said shoe.

2. An apparatus as claimed in claim 1 wherein said hinge connection means is removably connected to said back-part of said shoe.

3. An apparatus as claimed in claim 1 wherein said hinge connection means comprises a leather-like sheath which contains the bottom of said shank and projects downwardly therefrom to form a hinge section, said hinge section comprising one operative half of a snap button set, the other operative half of said snap button set being disposed proximate the apex of the heel curve of said shoe on said back part.

4. An apparatus as claimed in claim 1 wherein said attachment means comprises an adjustment means, said adjustment means providing each said strap with means of supporting said forepart selectively to a greater and lesser extent.

5. An apparatus as claimed in claim 1 wherein said attachment means is a hook-and-eye set, a hook of said hook-and-eye set being disposed on the outside of each forward extending portion and at least one eye of said hook-and-eye set being disposed proximate said upper end of each said strap.

6. An apparatus as claimed in claim 1 wherein said affixing means detachably connects said elastic strap to said forepart.

7. An apparatus as claimed in claim 1 wherein said affixing means is a snap button set comprising a first operative half and at least two second operative halves, said lower portion of each said strap comprising said first operative half, said fore part comprising said two second operative halves, one operative half of said two second operative halves disposed on the left side of said shoe and one operative half of said two operative halves disposed on the right side of said shoe.

8. A kit for an ankle-foot orthosis comprising:

a preformed brace;

and a belt;

said preformed brace comprising a narrow lower section and an upper section, said lower section comprising a bottom and a top, said lower section further comprising a hinge disposed proximate said bottom, said hinge comprising at least part of a connector means for connecting said preformed brace to a back exterior of a shoe above said shoe's heel, said lower section yet further comprising a belt and means for affixing said belt to said brace, both said belt and said means for affixing said belt to said brace disposed proximate said top of said lower section, said preformed brace further comprising an upper section connected to and vertically extending upwardly from said top of said lower section, said upper section curved so as to accept and generally conform to a calf of a user, said upper section comprising left and right portions, said left portion disposed to the left of said calf and projecting forward of said calf, is said right portion disposed to the right of said calf and projecting forward of said calf.

9. A kit as claimed in claim 8 further comprising means for attaching to said back of said shoe on an exterior of said shoe a further part of said connector means which operatively cooperates with said connector means of said hinge to connect said hinge to said back of said shoe.

10. A kit a claimed in claim 8 further comprising:

two adjustable attachment means, and two straps;

one said adjustable attachment means disposed on said left portion, one said adjustable attachment means disposed on said right portion;

each said strap comprising a flexible upper portion, an elastic portion, and a flexible lower portion, said flexible upper portion comprising means which cooperates with a respective adjustable attachment means for adjustable attachment of said flexible upper portion selectively to a right and left portion, said elastic portion connected to a bottom of said flexible upper portion and extending downwardly therefrom, said flexible lower portion connected to the bottom of said elastic portion and extending downwardly therefrom, said flexible lower section comprising at least part of an affixing means for detachably affixing said flexible lower section to said shoe, on said shoe's exterior.

11. A kit as claimed in claim 10 further comprising means for attaching to an exterior of a forepart of said shoe a further part of said affixing means which operatively cooperates with said affixing means of said flexible lower section to connect said lower section to said forepart of said shoe.

12. An ankle-foot orthosis comprising:

a shoe;

and a brace, said shoe comprising a heel and an upper, said upper comprising a forward part, a rearward part, an exterior, and two sides, said exterior comprising an outer surface of said upper, said two sides comprising a left side and a right side, said left side comprising part of said upper to the left of a vertical longitudinal plane bisecting said shoe into two halves, said right side comprising part of said upper to the right of said vertical longitudinal plane bisecting said shoe into said two halves, said upper further comprising two first balls of a first snap button set, each first ball of said first snap button set permanently attached to said exterior, each first ball disposed on said forward part on a respective side of said two sides, said upper yet further comprising two second balls of a dual snap button set, each second ball of said dual snap button set permanently attached to said exterior, disposed on said rearward part on a respective side of said two sides, proximate said heel curve;

at least part of said brace for receiving a calf, said brace comprising an inside and an outside,
- said inside being a side of said brace which faces toward said calf,
- said inside comprising a smooth finish,
- said outside being a side of said brace which faces away from said calf, said brace comprising a preformed vertical member of thin-sheeted plastic,
- said vertical member comprising an upper section, a lower section and two straps,
  - said upper section comprising a laterally curved part which accepts at least part of said calf,
  - said laterally curved part comprising two ends, one said end of said two ends respectively disposed to the left of said calf, one said end of said two ends respectively disposed to the right of said calf,
    - each said end comprising a forward extending portion which extends forward of said calf,
      - each said forward extending portion comprising a hook disposed on said outside,
  - each strap of said two straps comprising an upper part, an elastic part, and a lower part,
    - said upper part comprising a flexible durable material, an first upper end and a first lower end,
    - said upper part further comprising a plurality of vertically disposed eyes, each eye comprising a diameter which accepts each said hook,
    - said upper part detachable connected to said brace via cooperative connection of one eye of said plurality of eyes to said hook of a respective said forward extending portion,
    - said elastic part comprising an elastic durable material, a second upper end and a second lower end,
      - said second upper end permanently attached to said first lower end,
    - said elastic part extending downwardly from said first lower end,
    - said lower part comprising a flexible durable material, a third upper end and a third lower end,
      - said third upper end permanently attached to said second lower end,
    - said lower part extending downwardly from said second lower end,
    - said lower part further comprising a first socket of a first snap button set,
      - said lower part detachable connected to said shoe via cooperative connection of said first socket with said first ball attached to said respective side of said shoe,
  - said upper section joining to said lower section at said upper section's bottom end,
- said lower section being narrow and vertically elongated,
- said lower section comprising a belt and a pivoting connector,
  - said belt removably attached to the outside of said lower section proximate the top end of said lower section,
  - said belt providing means for securing said brace to said calf,
  - said pivoting connector comprising a leather-like sheath which contains said lower section's bottom end and extends downwardly therefrom to form a hinge,
    - said hinge comprising two second sockets of a dual snap button set,
    - said hinge detachable connected to said shoe via cooperative connection of said two second sockets with said second balls of said dual snap socket set attached to said rearward part of said shoe.

\* \* \* \* \*